United States Patent
Edwards

(10) Patent No.: US 6,900,630 B2
(45) Date of Patent: May 31, 2005

(54) AZIMUTHAL NMR IMAGING OF FORMATION PROPERTIES FROM A WELLBORE

(75) Inventor: Carl M. Edwards, Katy, TX (US)

(73) Assignee: Baker Hughes Incorporated, Houston, TX (US)

(*) Notice: Subject to any disclaimer, the term of this patent is extended or adjusted under 35 U.S.C. 154(b) by 16 days.

(21) Appl. No.: 10/717,123

(22) Filed: Nov. 19, 2003

(65) Prior Publication Data

US 2004/0130324 A1 Jul. 8, 2004

Related U.S. Application Data

(60) Provisional application No. 60/427,630, filed on Nov. 19, 2002.

(51) Int. Cl.[7] .................................................. G01V 3/00
(52) U.S. Cl. ...................................... 324/303; 324/314
(58) Field of Search ................................. 324/303, 314, 324/300, 306, 307, 309, 312, 318, 322

(56) References Cited

U.S. PATENT DOCUMENTS

| | | |
|---|---|---|
| 3,124,741 A | 3/1964 | Primas ........................ 325/0.5 |
| 4,307,343 A | 12/1981 | Likes .......................... 324/307 |
| 4,646,020 A * | 2/1987 | Brown ........................ 324/303 |
| 4,717,877 A | 1/1988 | Taicher et al. .............. 324/303 |
| 5,055,787 A | 10/1991 | Kleinberg et al. ........... 324/303 |
| 5,415,163 A * | 5/1995 | Harms et al. ................ 600/410 |
| 5,488,342 A | 1/1996 | Hanley ........................ 335/306 |
| 5,646,528 A | 7/1997 | Hanley ........................ 324/303 |
| 5,977,768 A | 11/1999 | Sezginer et al. ............. 324/303 |
| 6,023,164 A | 2/2000 | Prammer ..................... 324/303 |
| 6,166,540 A * | 12/2000 | Wollin ......................... 324/300 |
| 6,255,817 B1 | 7/2001 | Poitzsch et al. ............. 324/303 |
| 6,291,995 B1 | 9/2001 | Speier et al. ................ 324/303 |
| 6,326,784 B1 | 12/2001 | Ganesan et al. ............. 324/303 |
| 6,429,654 B1 | 8/2002 | Itskovich et al. ........... 324/314 |

* cited by examiner

Primary Examiner—Louis Arana
(74) Attorney, Agent, or Firm—Madan, Mossman & Sriram, P.C.

(57) ABSTRACT

A method and apparatus for performing NMR measurements suppressing contribution to NMR signals from within the borehole. Within the region of examination, the RF magnetic field has a spatially varying intensity. NMR signals (free induction decay or spin echo signals) are inverted to give spin density as a function of field intensity. This inversion is then mapped to spatial positions using the known RF field variation. The effect of signals arising from within the borehole can be suppressed. It is also possible to obtain an azimuthal image of the spin density.

31 Claims, 9 Drawing Sheets

AZIMUTHAL NMR IMAGING OF FORMATION PROPERTIES FROM A WELLBORE

CROSS-REFERENCES TO RELATED APPLICATIONS

This application claims priority from U.S. Provisional Patent Application Ser. No. 60/427,630 filed on Nov. 19, 2002.

BACKGROUND OF THE INVENTION

1. Field of the Invention

The invention is in the field of Nuclear Magnetic Resonance testing equipment. In particular the invention is an apparatus for NMR testing for azimuthal imaging of formation properties in borehole drilling.

2. Description of the Related Art

A variety of techniques have been used in connection with wellbore drilling to determine the presence of and to estimate quantities of hydrocarbons (oil and gas) in earth formations surrounding the wellbore. These methods are designed to determine formation parameters (in this application called "parameters of interest") including, among other things, porosity, fluid content and permeability of the rock formation. Typically, the tools designed to provide the desired information are used to log the wellbore. Much of the logging is done after the wellbore has been drilled. Removing the drilling apparatus in order to log the wellbore can prove costly in terms of time and money. More recently, wellbores have been logged simultaneously with drilling of the wellbores, which is referred to as measurement-while-drilling ("MWD") or logging-while-drilling ("LWD"). Measurements have also been made when tripping a drillstring out of a wellbore. This is called measurement-while-tripping ("MWT").

One recently evolving technique involves utilizing Nuclear Magnetic Resonance (NMR) logging tools and methods for determining, among other things, porosity, hydrocarbon saturation, and permeability of the rock formations. The NMR logging tools are utilized to excite the nuclei of the fluids in the geological formations in the vicinity of the wellbore so that certain parameters such as spin density, longitudinal relaxation time (generally referred to in the art as "$T_1$"), and transverse relaxation time (generally referred to as "$T_2$") of the geological formations can be estimated. From such measurements, porosity, permeability, and hydrocarbon saturation are determined, which provides valuable information about the make-up of the geological formations and the amount of extractable hydrocarbons.

NMR well logging instrument typically include a permanent magnet to induce a static magnetic field in the earth formations and a transmitting antenna, positioned near the magnet and shaped so that a pulse of radio frequency ("RF") power conducted through the antenna induces an RF magnetic field in the earth formation. The RF magnetic field is generally orthogonal to the static magnetic field. After an RF pulse, voltages are induced in a receiving antenna by precessional rotation of nuclear spin axes of hydrogen or other nuclei about the static magnetic field. The precessional rotation occurs in an excitation region where the static magnetic field strength corresponds to the frequency of RF magnetic field. A sequence of RF pulses can be designed to manipulate the nuclear magnetization, so that different aspects of the NMR properties of the formation can be obtained.

For NMR well logging the most common sequence is the CPMG sequence that comprises one excitation pulse and a plurality of refocusing pulses. The region of interest for these NMR methods generally lies totally within the rock formation. However, the sensitive volume, as defined by the magnitude of the static magnetic field and the frequency of the RF magnetic field can lie within the borehole, thus producing erroneous signals. Due to differing geometries of boreholes, different methods of NMR logging have been devised. For a small axially symmetric borehole in which the probing device is centrally located, it is possible to obtain information from an axially symmetric region within the rock formation.

A problem of interest in NMR logging is that of obtaining azimuthal information about earth formations surrounding a borehole. U.S. Pat. No. 5,977,768 to Sezginer, et al. teaches the use of a segmented antenna for obtaining such information. The static magnetic field is produced by a pair of opposed magnets with magnetization parallel to the longitudinal axis of the tool. The region of examination is a toroidal zone around the borehole. By the use of segmented antennas, each antenna receives signals primarily from a quadrant. U.S. Pat. No. 6,255,817 to Poitzsch, et al. teaches a method for analysis of data from the Sezginer device. U.S. Pat. No. 6,326,784 to Ganesan, et al. discloses an arrangement in which gradient coils are used to suppress spin-echo signals for portions of the region of examination. As would be known to those versed in the art, the toroidal region defined by the opposed magnet configuration is generally smaller than that of a transverse-dipole magnet arrangement. This feature restricts the region from which signals are obtained and further lowers the signal level An apparently unrelated problem arises with tools using a transverse dipole magnet configuration. An example of this is in a "side-looking" NMR tool that is sensitive to NMR excitation on one side of the tool and less sensitive to NMR excitation on the other side. The more sensitive side of the tool is typically pressed against the sidewall of a borehole adjacent a formation, thereby providing minimum separation between the NMR tool's RF field generating assembly and the formation volume of NMR investigation. The less sensitive side of the tool is thus exposed to the borehole. This operational NMR technique is most effective when the borehole diameter is much greater than the diameter of the NMR tool.

Typically, side-looking NMR tools set up static and RF magnetic field distributions in a particular relationship to achieve maximum NMR sensitivity on one side of the NMR tool. These conventional side looking NMR techniques are well known in the art, as taught in the following patents: U.S. Pat. No. 4,717,877 to Taicher, et al., U.S. Pat. No. 5,055,787 to Kleinberg, et al., U.S. Pat. No. 5,488,342 to Hanley, U.S. Pat. No. 5,646,528 to Hanley, and U.S. Pat. No. 6,0213,164 to Prammer, et al.

The Kleinberg '787 patent teaches a side-looking NMR tool which generates a static magnetic field which results in a sensitive volume on only the front side of the tool. The sensitive region in front of this tool generates a field having a substantially zero gradient, while the region behind this tool has a relatively large gradient field. Consequently, the volume of the sensitive NMR region in front of the tool is much larger and contributes more significantly to the composite NMR signal, than does the NMR region behind the tool. The '787 patent technique, however, is only practical when the sensitive volume in front of the tool is very close to the tool. This condition therefore limits the available depth of NMR investigation. The '787 tool design also requires a substantially zero gradient in the sensitive volume. Such a zero gradient is not always desirable, however, in NMR well logging, as a number of associated NMR techniques depend upon having a finite, known gradient within the NMR sensitive volume.

The Hanley '342 patent teaches a NMR tool technique which provides a homogeneous region localized in front of the tool. The '342 tool design overcomes the disadvantageous requirement of the sensitive volume being undesirably close to the NMR tool. However, it suffers because the sensitive volume is not elongated along the longitudinal axis of the NMR tool or bore hole axis, causing unacceptable errors due to motional effects.

Hanley '528 discloses another variation of the Jackson device in which a shield of electrically conductive material is positioned adjacent to and laterally offset from the set of electrical coils whereby the magnetic field generated by the RF antenna is asymmetrically offset from the axis of the magnets. The region of uniform static field remains a toroid, as in the Jackson device. The Hanley '528 device may be operated eccentrically within a large borehole with a reduction in the borehole signal. Both of the Hanley devices suffer from the drawback that the axial extent of the region of examination is small, so that they cannot be operated at high logging speeds.

There are several devices in which the problem of limited axial extent of the basic Jackson configuration of permanent magnets is addressed. U.S. Pat. No. 4,717,877 to Taicher, et al. teaches the use of elongated cylindrical permanent magnets in which the poles are on opposite curved faces of the magnet. The static field from such a magnet is like that of a dipole centered on the geometric axis of the elongated magnets and provides a region of examination that is elongated parallel to the borehole axis. The RF coil in the Taicher device is also a dipole antenna with its center coincident with the geometric axis of the magnet, thereby providing orthogonality of the static and magnetic field over a full 360° azimuth around the borehole.

U.S. Pat. No. 6,023,164 to Prammer discloses a variation of the Taicher patent in which the tool is operated eccentrically within the borehole. In the Prammer device, NMR logging probe is provided with a sleeve having a semi-circular RF shield covering one of the poles of the magnet. The shield blocks signals from one side of the probe. The probe is provided with elements that press the uncovered side of the probe to the sidewall of the borehole so that signals received by the uncovered side arise primarily from the formation.

For both the Prammer '164 and the Hanley '528 devices, in order to get the best attenuation in the field behind the probe while maintaining sensitivity in front of the probe, the shield should be positioned as far away from the front region as possible. The effectiveness of the shield is limited by the diameter of the tool. In the absence of a shield, the Prammer '164 and Hanley '528 tools have a circular sensitive region, so that use of either device in an eccentric manner would result in a large signal from the borehole fluid.

The passive RF shield is typically positioned as far as possible from the front region in order not to spoil NMR tool sensitivity in the desired region and as close as possible to the back region for maximum effectiveness. It can be seen therefore that the effectiveness of the passive shield will eventually be limited by the diameter of the tool. If we can not achieve sufficient attenuation with a shield inside the tool we will have to adopt one of the following undesirable options: use the large magnet to move the rear region further away; reduce the signal from the front region; or place a shield outside the tool. Thus, neither approach presents a practicable solution.

U.S. Pat. No. 6,348,792 to Beard, et al., the contents of which are fully incorporated herein by reference, introduces a configuration of a primary static magnet with a secondary shaping magnet. The shaping magnet is used to shape the static magnetic field to conform to the RF field over a larger azimuthal sector around the tool. A shield in the back part of the device reduces the RF field behind the tool. The static and RF dipoles are rotated 90° relative to prior art, so that the static dipole points to the side of the tool and the RF dipole to the front of the tool. With this arrangement, eddy currents in the shield are substantially increased, increasing its effectiveness. U.S. Pat. No. 6,445,180 of Reiderman, et al., having the same assignee and the contents of which are fully incorporated herein by reference, teaches the use of a primary and secondary antenna system with the tool of the Beard patent. The primary antenna, being the larger of the two, creates a volumetrically extended magnetic field, most of which extends into the rock formation, and some of which lies within the borehole. The secondary antenna acts synchronously with the primary antenna, but its current circulates in a direction opposite to the direction of the current in the primary antenna, causing a magnetic field that cancels the magnetic field of the primary antenna in the region inside the borehole, thereby significantly reducing contributions from the borehole to the sensed NMR signal.

A limitation of these particular applications is that the device has only a side-looking mode, which is useful for large boreholes. However, for small boreholes, it is advantageous to use a central mode which excites signals on all sides of the NMR tool. Logging of boreholes with different diameters would thus require the use of different tools and an associated increase in costs due to having a larger inventory of tools. U.S. Pat. No. 6,525,535 of Reiderman, et al., having the same assignee as the present application and the contents of which are fully incorporated herein by reference, teaches a method and device similar to that in the Reiderman '180 patent in which the secondary antenna may be used as a booster antenna in small boreholes. This makes it possible to use the same logging tool for a variety of borehole sizes.

However, when the borehole is very large, the device of the Reiderman '451 application may not be able to fully suppress signals from the borehole. This situation is illustrated in FIGS. 3a and 3b. The FIG. 3a shows a logging tool 311 disposed in a borehole 301. The tool is shown in the side-looking mode and the region of examination is denoted by the combination of 321, 323a and 323b. By use of the hardware compensation (which may include a spoiler antenna and the arrangement of the basic magnet and antenna configuration, none of which are shown in the figure), signals from the region 325 within the borehole are suppressed.

FIG. 3b shows the same logging tool 311 in a much larger borehole 301. As can be seen, a portion of the region of examination denoted by 323a and 323b now lies within the borehole. The borehole fluid includes a large quantity of water, so that the signal from the borehole fluid could be much larger than those from the formation. A similar problem occurs even in smaller boreholes with a large amount of washout. It would therefore be desirable to suppress signals from within the borehole using a method other than hardware compensation: this would make it possible to use the same logging tool in a much larger range of borehole sizes. This suppression of signals from a selected azimuthal sector is, in principle, the same problem discussed above with respect to azimuthal imaging of the formation. The present invention is directed towards a solution of this problem.

SUMMARY OF THE INVENTION

The present invention is a method of determining a parameter of a region of interest of an earth formation using a nuclear magnetic resonance (NMR) logging tool conveyed in a borehole. A magnet on the logging tool is used for producing a static magnetic field in a region including said region of interest. A sequence of selected radio frequency (RF) pulses is used for producing an RF magnetic field in said region and signals indicative of the parameter of interest are obtained. In one embodiment of the invention, the RF pulses have pulse lengths related to zeros of a Bessel function and the signals are free induction decays. In an alternate embodiment of the invention, the RF pulses comprise an excitation pulse followed by a plurality of refocusing pulses, the lengths of the excitation pulses being related to zeros of a Bessel function, and the signals are spin-echo signals.

With either embodiment of the invention, by applying a inverse Hankel transform, the spin property is obtained as a function of the RF magnetic field strength. From knowledge of the RF magnetic field distribution, the spatial spin distribution can be recovered. Specifically, a differentiation can be made between spins within and outside the borehole, as well as an azimuthal distribution of the spins.

Figure 2:
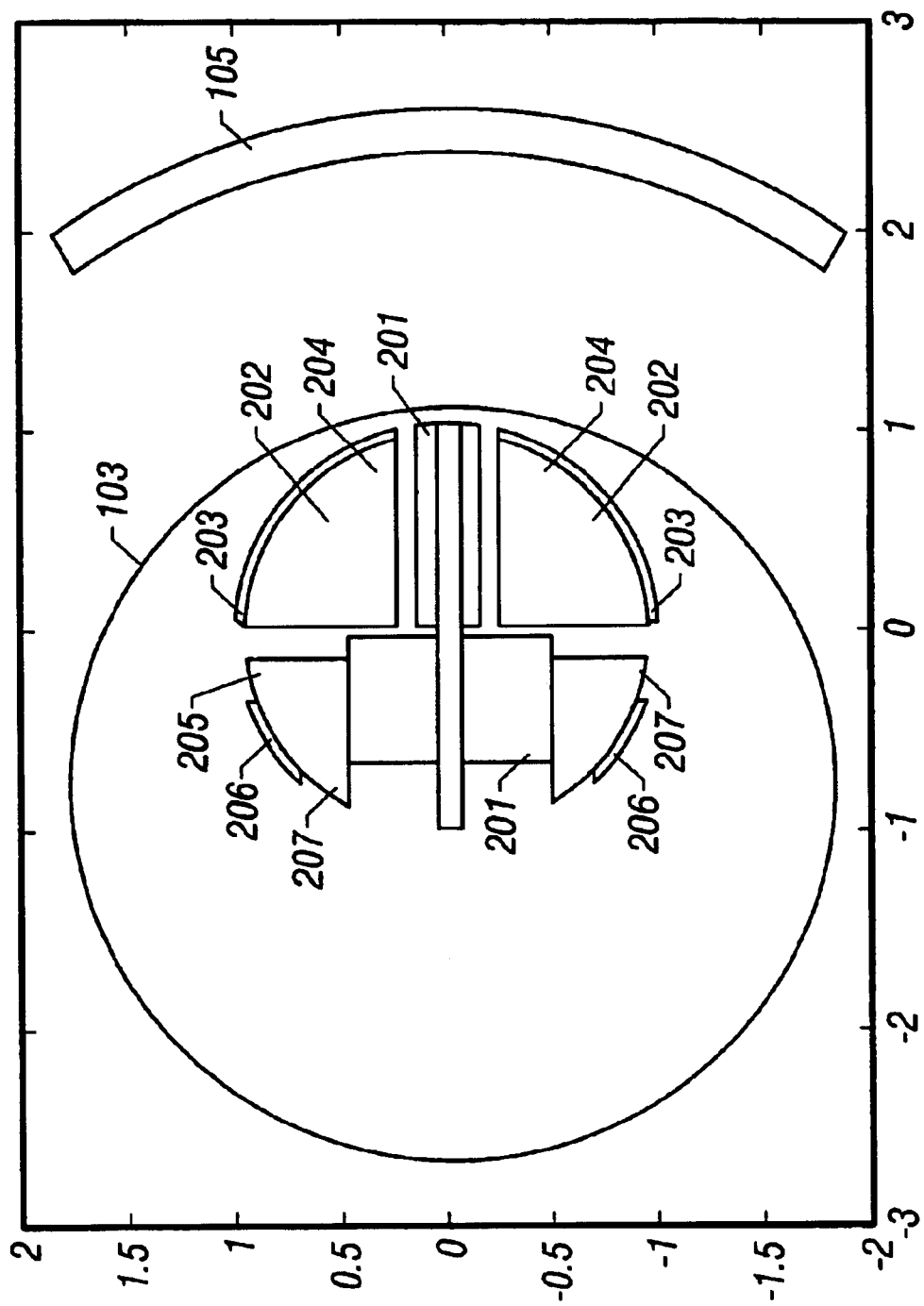
Figure 3A:
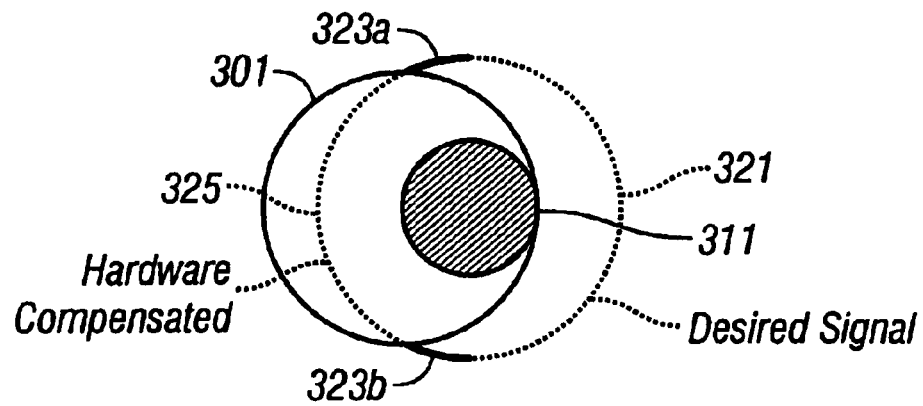
Figure 3B:
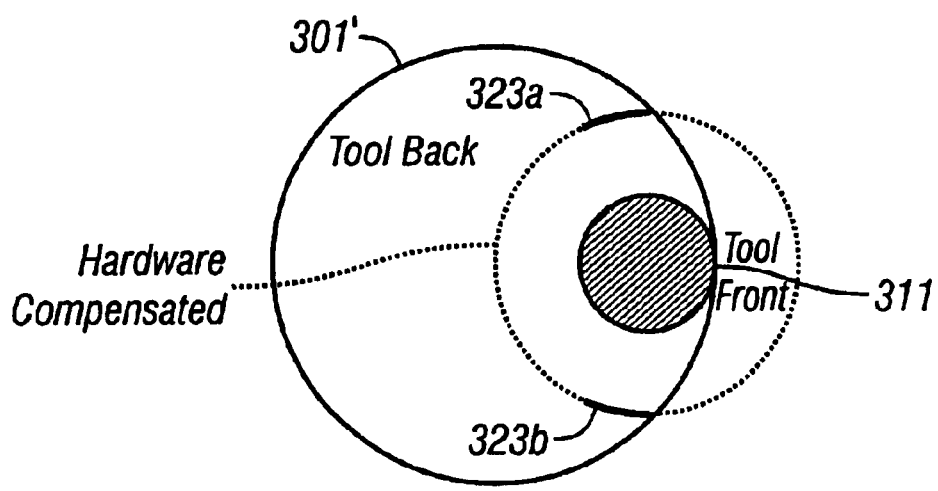
Figure 4:
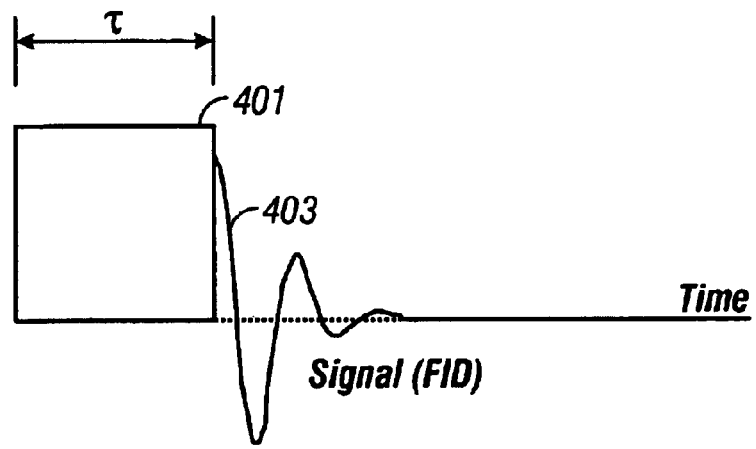
Figure 5A:
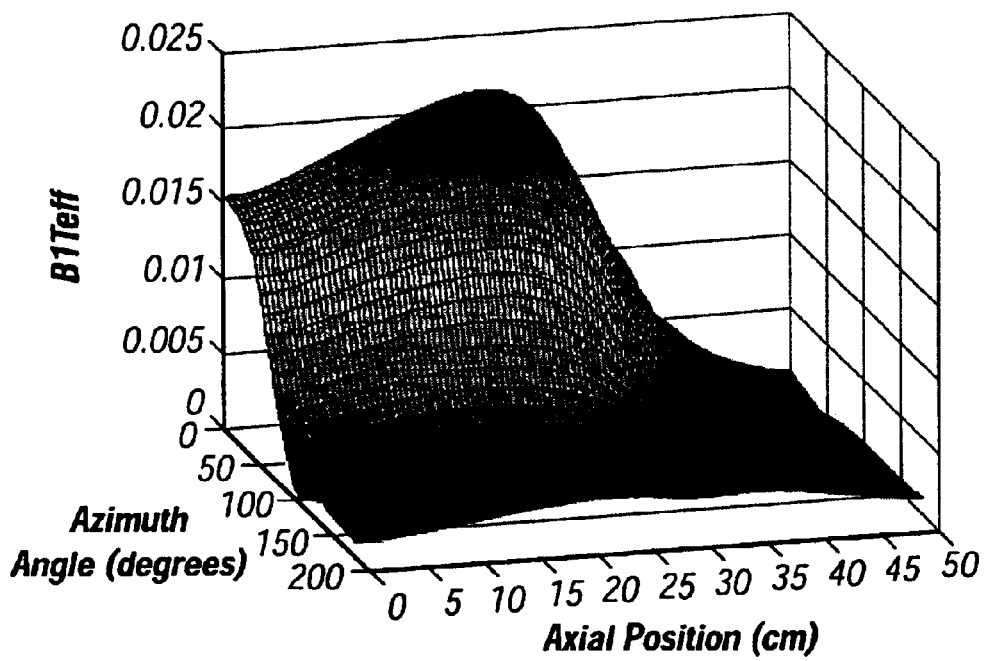
Figure 5:
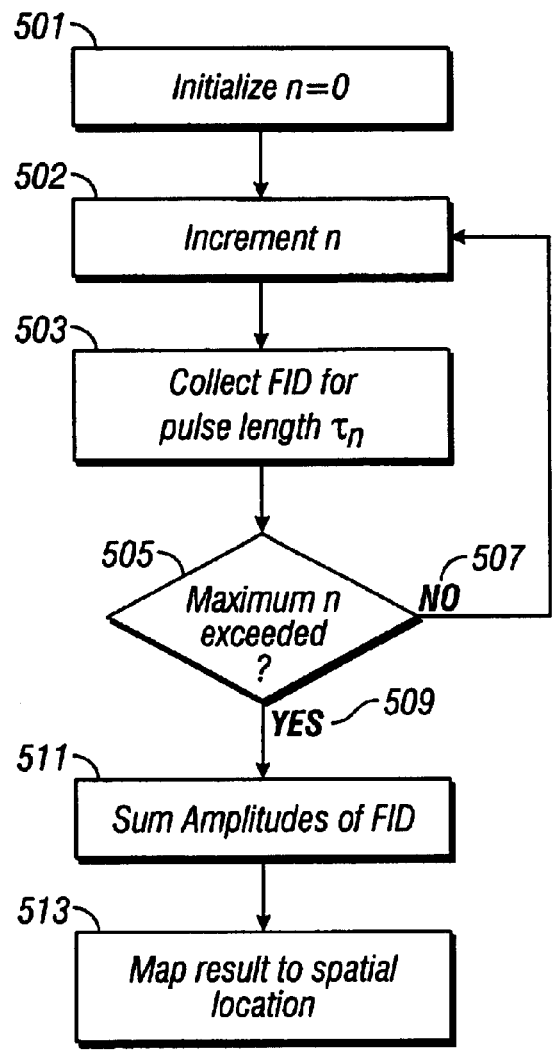
Figure 6:
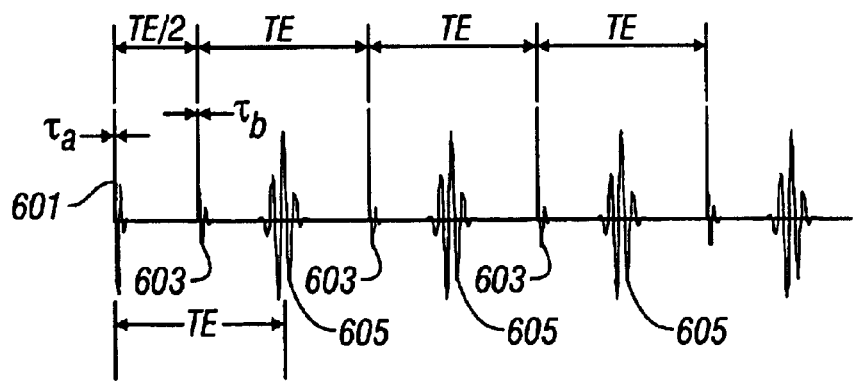
Figure 5B:
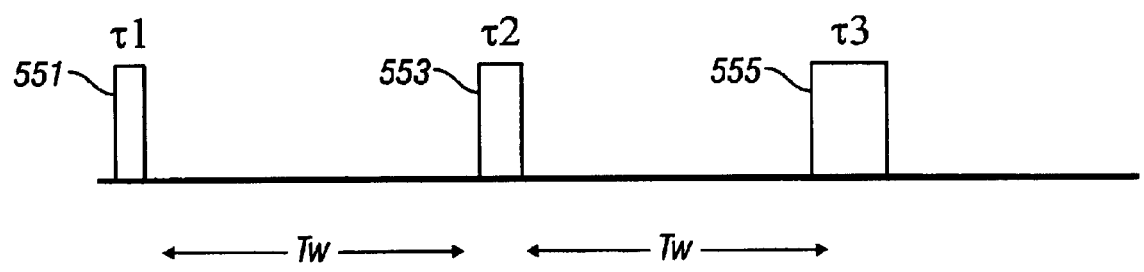
Figure 5C:
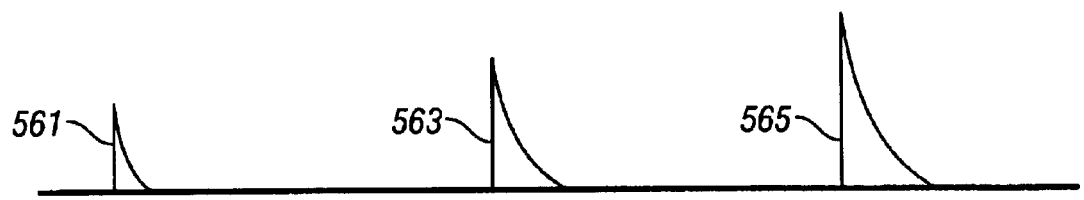
Figure 7A:
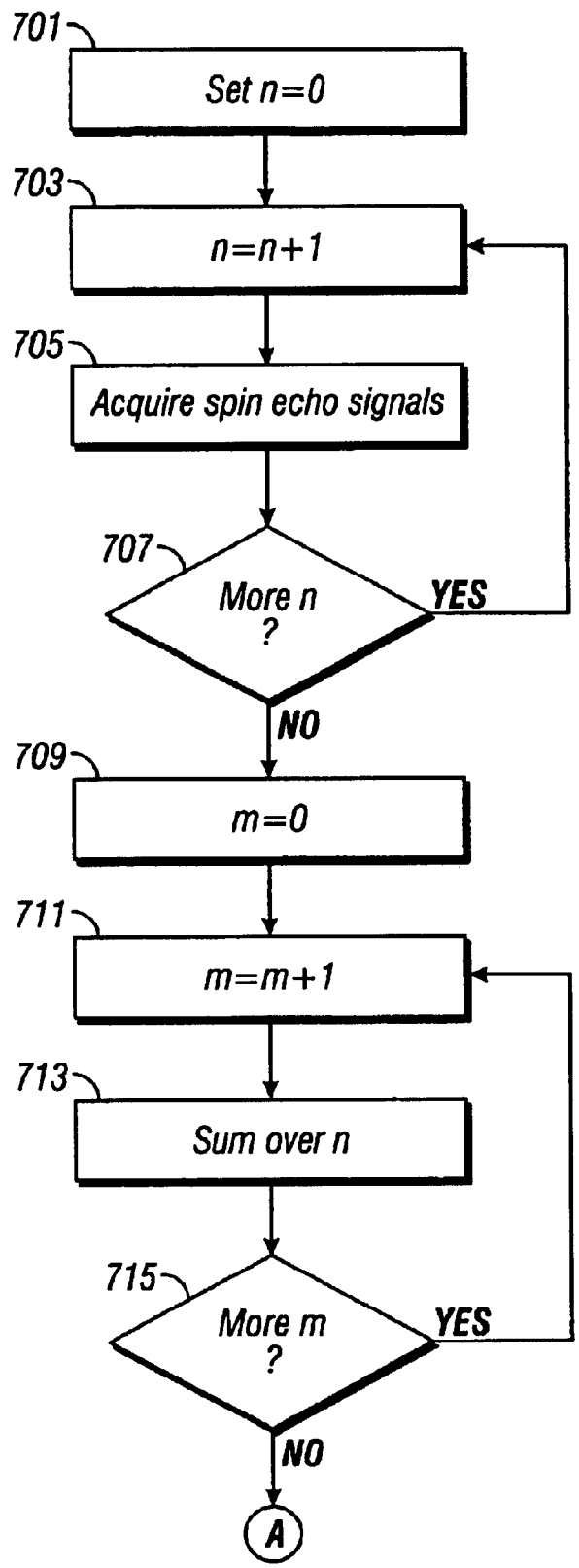
Figure 7B:
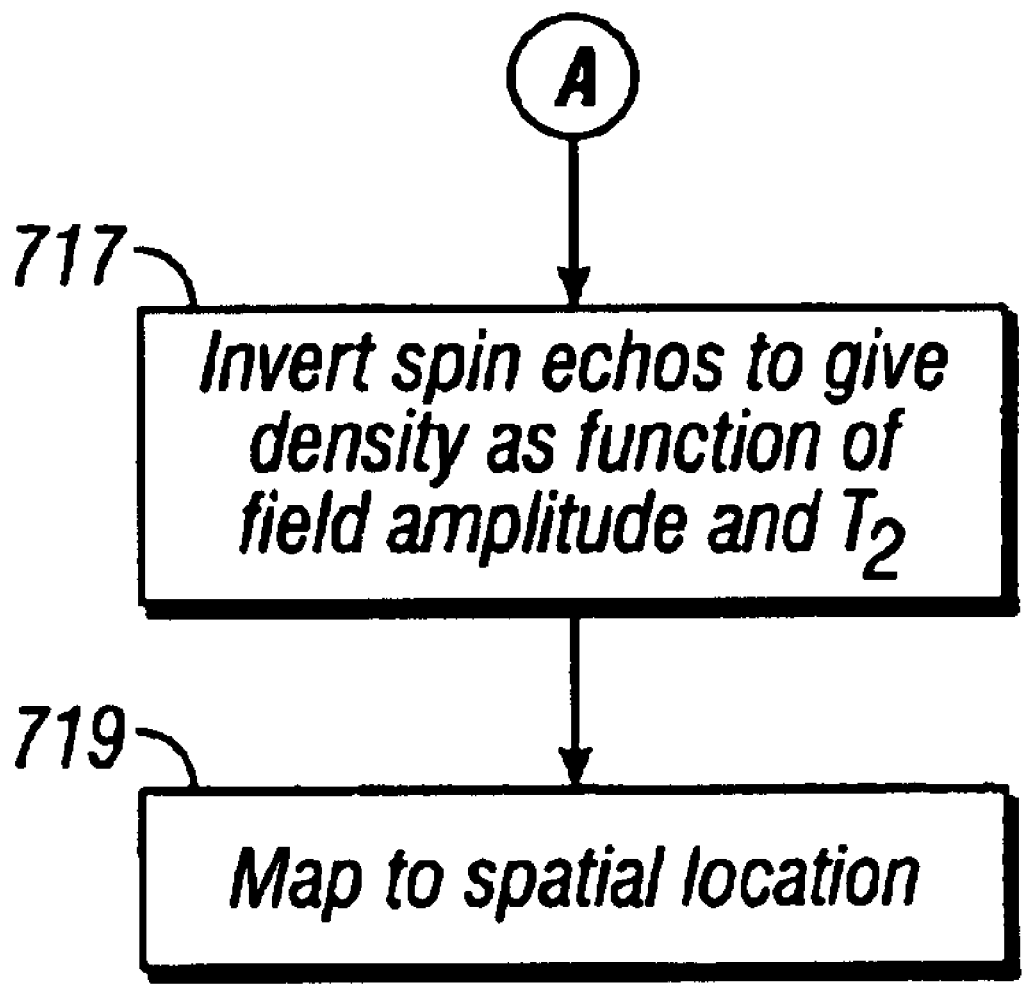
Figure 7C:
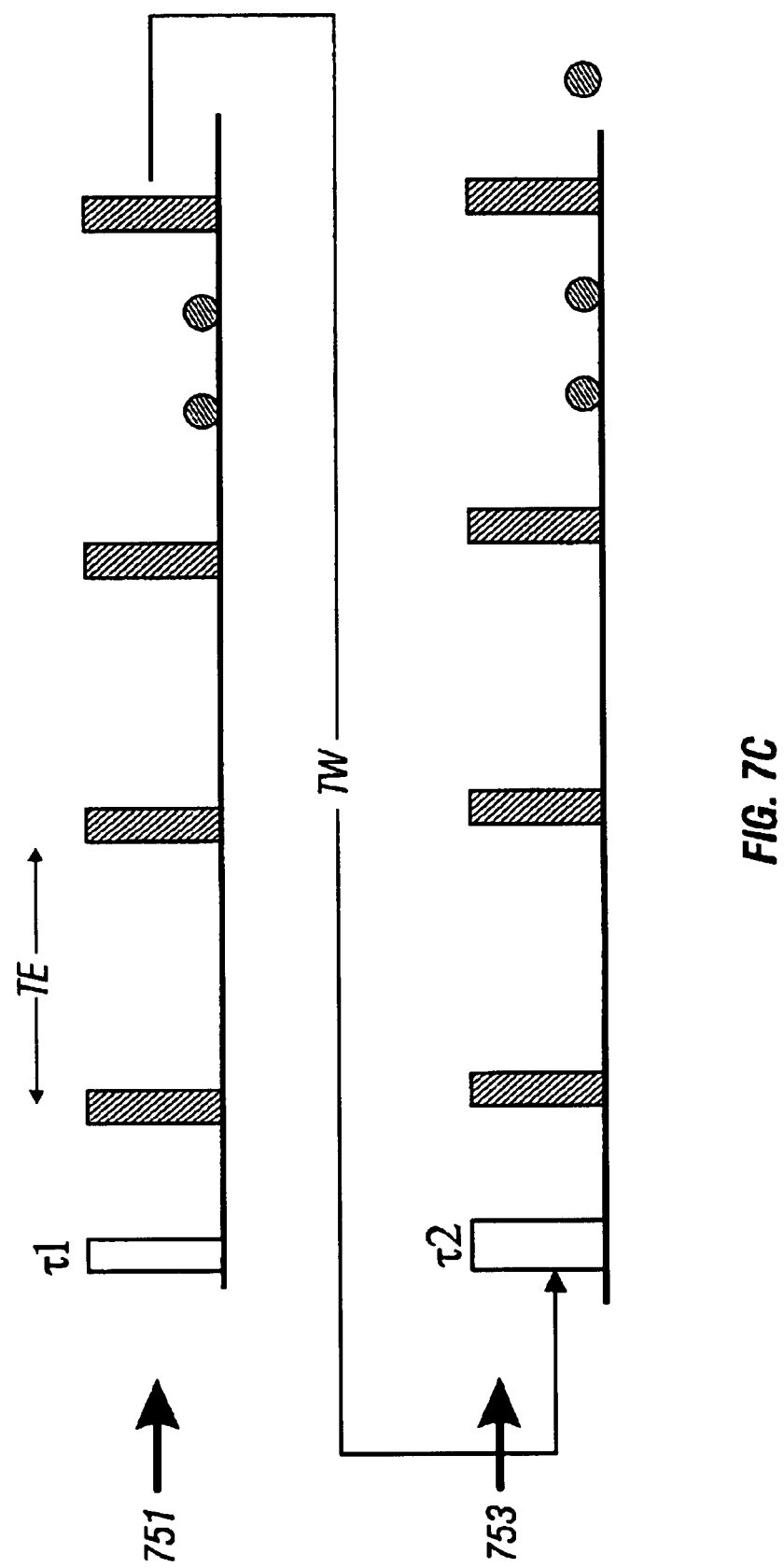

FIG, 2 (Prior Art) is a schematic illustration showing the use of a RF spoiler antenna;

FIGS. 3a and 3b shows a problem associated with logging in large diameter boreholes;

FIG. 4 shows a free induction decay following a RF pulse;

FIG. 5 is a flow chart illustrating a first embodiment of the present invention for determination of longitudinal relaxation times;

FIG. 5a is an illustration of the RF field distribution for the tool configuration of FIG. 2;

FIG. 5b shows an exemplary pulse sequence for one embodiment of the invention;

FIG. 5c shows free induction decays corresponding to the pulse sequence of FIG. 5b;

FIG. 6 shows modified CPMG sequences according to a second embodiment of the invention for determination of transverse relaxation times;

FIGS. 7a and 7b show a flow chart illustrating a second embodiment of the present invention for determination of transverse relaxation times; and FIG. 7c shows a pulse sequence suitable for use with the embodiment of the invention depicted in FIG. 7b.

DETAILED DESCRIPTION OF THE INVENTION

Figure 1:
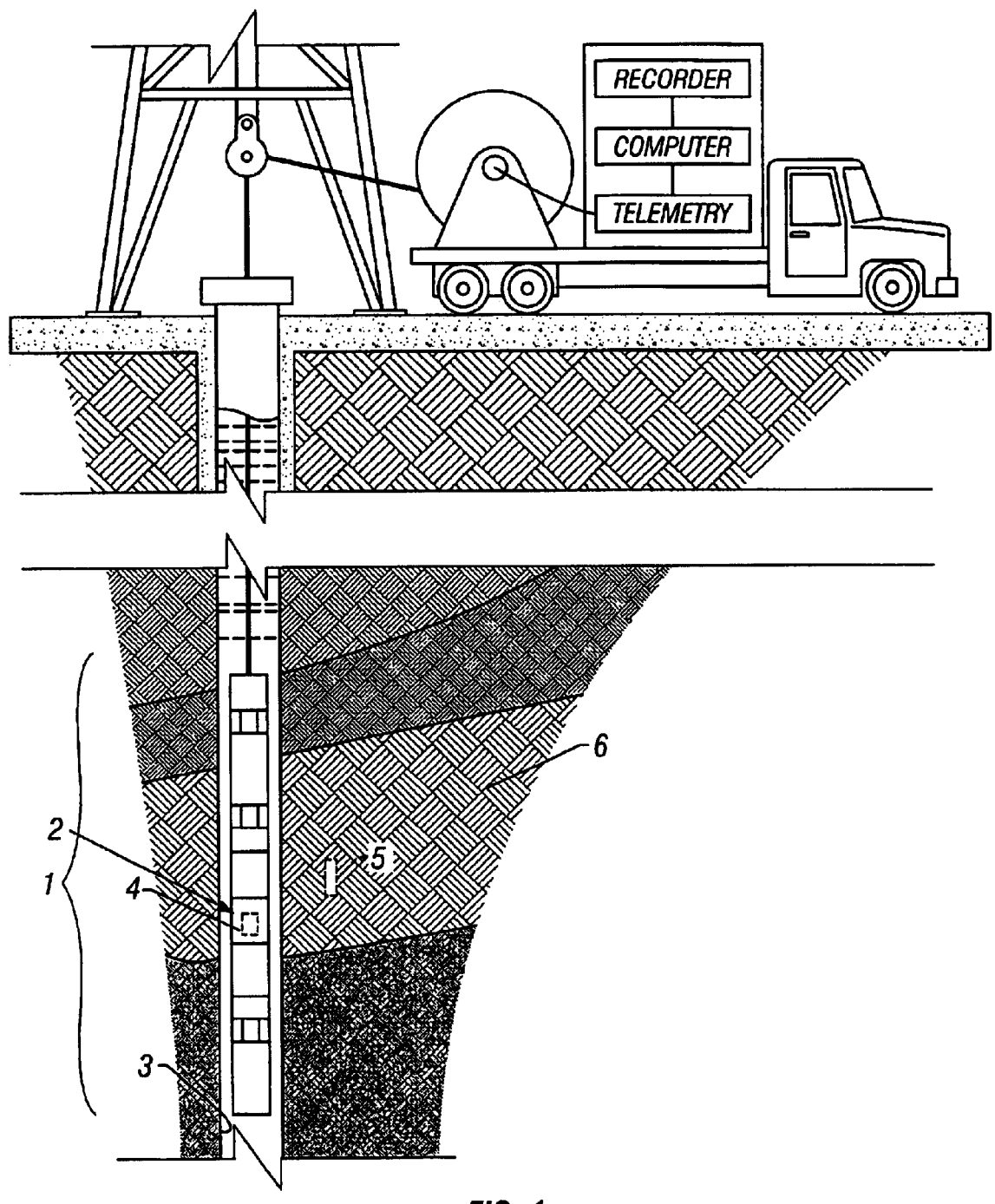
FIG. 1 (Prior Art) shows a side-looking well logging tool as it is typically used in a borehole penetrating earth formation.

FIG. 1 (Prior Art) shows a well logging NMR tool suitable for use with the method of the present invention. The logging tool 102 deployed is in borehole 103 penetrating earth formations 107, 108, 109 for making measurements of properties of the earth formations. The borehole 103 in FIG. 1 is typically filled with a fluid known in the art as "drilling mud." The side-looking tool has antenna assembly 104 for generating NMR excitation pulses in a region of investigation 105 and receiving NMR signal from the region 105 in formation 107, 108, 109 adjacent borehole 103. The region of investigation 105 is to one side of the tool. The processing of data may be done by a surface computer or may be done by a downhole processor.

FIG. 2 (Prior Art) shows the cross-section of the preferred NMR probe perpendicular to the longitudinal axis of the NMR tool, which is typically parallel to the borehole 103 axis. The magnet assembly 201 induces a required distribution of a static magnetic field in a region of interest 105 in the formation, adjacent borehole 103. The main RF antenna assembly 202 generates a RF magnetic field in the region of interest in the transmit mode and receives the NMR signal from the excitation region of the formation (the region of interest) in the receive mode. The first antenna assembly, the main RF antenna comprises an antenna winding 203 and a soft magnetic core 204 to improve the first antenna efficiency in both the transmit and receive modes. In large boreholes, the second antenna assembly 205 serves as an active spoiler comprising winding 206 and preferably a soft magnetic core 207 to improve the efficiency of the spoiler. The antenna and spoiler winding can be either one turn flat wire or multi-turn winding. This arrangement works well in boreholes of diameter 12" (30 cm) or so. In smaller boreholes (typically less than 8" diameter), the second antenna assembly may be used in a boost mode as described in Reiderman '451.

As discussed above, in very large boreholes with diameter greater than about 12.25" (30.75 cm) or so or in smaller boreholes with moderate to severe washouts, a considerable amount of the region of examination is within the borehole. The method of the present invention is directed towards correcting for the effects of this signal. The method is also applicable to determination of azimuthal variation in properties of the earth formation.

The present method is based upon rotating frame zeugmatography. Hoult (1979) first described the technique called rotating frame zeugmatography. He described two methods. The first method phase encodes the position of the spins and the other encodes position of the spins in the amplitude of the signal. In the first method, the magnetization evolves under a spatially variant radio-frequency magnetic field. The magnetization is tipped into the xy-plane of the rotating frame by a 90° pulse with no spatial gradient. At this point the phase of the magnetization in the rotating frame has a component that is proportional to the position. Changing the amplitude or length of time of the spatially variant RF magnetic field and collecting free induction decay signals (FIDs) after the 90° pulse is the next step in this imaging technique. These are then Fourier transformed to produce an image.

The second method described is relevant to the instant invention. Instead of phase encoding the position, the position is encoded in the amplitude of the FID. Here the tip angle is a function of the magnitude of the RF field. The pulse width is changed and the FIDs are collected. The amplitudes are a Fourier sine transform of location.

FIG. 4 illustrates the technique of amplitude rotating frame zeugmatography. For the following discussion, the narrow pulse approximation is used. As a result all resonant offset effects are negligible. The coil that supplies RF magnetic field applied during the pulse is shaped such that the RF magnetic field varies linearly over the sample in a given direction. Without loss of generality this direction can be labeled the x-axis. Thus the magnetic field is given by:

$$B_1(\vec{r}) = B_{10} + G_{1x}x \qquad (1)$$

where $B_{10}$ is a constant and $G_{1x}$ is the linear gradient in the RF magnetic pulse. After a pulse of length $\tau$ is applied, the amplitude of the FID signal is given by:

$$S(\tau) \propto \int_{vol} d^3r m(\vec{r}) \sin(\gamma(B_{10} + G_{1x}x)\tau) \qquad (2)$$

where the integration is performed over the volume of the sample. The integration over the y- and z-coordinates can be easily performed and the result is that the signal is the Fourier sine transform of the spin density projected along the x-axis as given by:

$$S(\tau) \propto \int_a^b dx m_\perp(x) \sin(\gamma(B_{10} + G_{1x}x)\tau) \qquad (2a)$$

where $m_\perp$ is the projection of the magnetization along a given axis (the x-axis in the present case). The limits of integration, a and b, are the maximum extent of the sample.

Applying the sine transform to eq. (2a) gives the following result:

$$\begin{aligned} S(\omega) &= \int_0^\infty d\tau \sin\omega\tau S(\tau) \qquad (2b) \\ &= \int_0^\infty d\tau \sin\omega\tau \int_a^b dx m_\perp(x) \sin(\gamma(B_{10} + G_{1x}x)\tau) \\ &\quad \int_a^b dx m_\perp(x) \int_0^\infty d\tau \sin\omega\tau \sin(\gamma(B_{10} + G_{1x}x)\tau) \\ &\propto \int_a^b dx m_\perp(x) \delta(\omega - \gamma(B_{10} + G_{1x}x)) \\ &= m_\perp\left(\frac{\omega - \gamma B_{10}}{\gamma G_{1x}}\right) \end{aligned}$$

Thus, the sine transform of $S(\tau)$ is proportional to the spin density projected onto the x-axis at $\omega = \gamma(B_{10} + G_{1x}x)$. The method of the present invention relies on the fact that with the preferred hardware configuration discussed above with reference to FIG. 2, the RF field varies from a maximum in front of the tool to near zero at the back. There are other magnet and coil configurations where there is a spatially-varying RF field over the sensitive volume, and the method of the present invention may be used with tools having such configurations.

The example described above can be generalized to an RF magnetic field that is an arbitrary function of the space variables. Substituting an arbitrary spatially varying RF magnetic field, $B_1 = B_1(x)$, for a linear field, $B_1 = B_{10} + G_{1x}x$, the Fourier sine transform in one dimension of the signals becomes:

$$\begin{aligned} S(\omega) &\propto \int d\tau \sin(\omega\tau) S(\gamma B_1(x)\tau) \qquad (3) \\ &= \int dx m(x) \delta(\omega - \gamma B_1(x)) \\ &= \sum_{n=1}^N \left(\gamma \frac{dB_1(x)}{dx}\bigg|_{x_n}\right)^{-1} \int dx m(x) \delta(x - x_n), \end{aligned}$$

where $x_n$ are the zeros of $\gamma B_1(x) - \omega$. This transform takes into account the known properties of the delta function of an arbitrary function. Thus, the transformed signal could contain the signal from many different locations if the RF magnetic field varies. dramatically. However, for a monotonic function there is a single zero at for each frequency with a corresponding location within the sample. Signals associated with small values of $B_1$ can be easily separated from those with large $B_1$.

The principle of the invention has been described above with respect to the FID. In a well logging environment, the excitation volume is band-limited. It is defined not by the volume of the coil but rather by the homogeneity or spatial distribution of the static magnetic field. The extent of the sensitive volume can be approximated by the following expression:

$$\Delta B_0/B_1 \leq 1, \qquad (4)$$

where $\Delta B_0$ is the difference between the static magnetic field and the field that corresponds to the RF operating frequency. Spins that are far off resonance do not contribute to the received signal and therefore are not included in the sensitive volume. Eq. (4) is only approximate and a more exact expression would require a detailed analysis of the well logging tool design. Accordingly, the narrow pulse approximation does not apply and off-resonance effects must be accounted for in the analysis of any pulse sequence.

Consider a single pulse followed by an FID as shown in FIG. 4. The reciprocity theorem (Hoult and Richards, 1976) gives the incremental voltage in the coil as a function of both the RF magnetic field and the magnetization. After some algebraic manipulation this relationship translates into the following expression (Hurlimann and Griffin, 2000):

$$S(t) \approx \frac{2\chi}{\mu_0 I}\omega_0^2 \int\int d\omega_1 d(\Delta\omega)\omega_1 f(\Delta\omega, \omega_1) m_{x,y}(\Delta\omega, \omega_1), \qquad (5)$$

where $\chi$ is the nuclear magnetic susceptibility, $\mu_0$ is the permeability of free space, I is the current in the coil, $\omega_1 = \gamma B_1$, and $\Delta\omega = \omega_0 - \gamma B$. The function, $f$, is the proton density at a given offset frequency and RF field amplitude. The quantities, $m_{x,y}$, are the components of the transverse magnetization normalized to one at equilibrium. B is the magnetic field and $\omega_0$ is the angular frequency of the RF magnetic field. Eq. (5) is to be integrated for all values of $\omega_1$ and $\Delta\omega$, but realistically the integration over $\Delta\omega$ may be limited to a few multiples of $\omega_1$.

Immediately following a pulse, the components of the transverse magnetization are given by the following (Morris, 1986):

$$m_x = \sin\theta \cos\theta(1 - \cos(\tau\sqrt{\omega_1^2 + \Delta\omega^2})),$$

$$m_y = \sin\theta \sin(\tau\sqrt{\omega_1^2 + \Delta\omega^2}) \qquad (5a),$$

where $$\tan\theta = \frac{\omega_1}{\Delta\omega}. \qquad (5b)$$

In the special case where $f(\Delta\omega, \omega_1)$ is independent of $\Delta\omega$ near resonance, such as a logging tool with a substantial radial gradient, then eqs. (5) and (5a) yield a simple expression for the amplitude immediately following the pulse after integrating over $\Delta\omega$. The in-phase portion, or x- component, of the magnetization integrates to zero while the y- or quadrature component integrates to:

$$S(\tau) \approx \frac{2\chi}{\mu_0 I} \omega_0^2 \int_0^{\omega_{1\max}} d\omega_1 \omega_1 f(\omega_1) \frac{\pi\omega_1}{\gamma G} J_0(\omega_1\tau), \qquad (6)$$

where G is the gradient of the static magnetic field, $J_0$ is the zero-order Bessel function and $\omega_{1max}$ is the maximum value of $B_1(x)$. If G is a constant and independent of $\omega_1$, then eq. (6) shows that the amplitude of the NMR signal is the finite Hankel transform of the product of the proton density as a function of the RF magnetic field amplitude and the RF amplitude itself. Because the Bessel functions are a complete set, the proton density as a function of RF field amplitude can be found using the inverse transform finite Hankel transform. Being careful to change variables, the following results:

$$\omega_1 f(\omega_1) = \frac{\mu_0 I \gamma G}{\pi \chi \omega_0^2 \omega_{1\max}^2} \sum_{n=1}^{\infty} \frac{S(\omega_{1\max}\tau_n)}{J_1^2(\omega_{1\max}\tau_n)} J_0(\omega_1\tau_n). \qquad (7)$$

Here the values of $\tau_n$ are related to the zeros of the zero-order Bessel function, $j_{0,n}$, as follows:

$$\omega_{1max}\tau_n = j_{0,n}. \qquad (8)$$

The inverse Hankel transform is implemented in practice as a summation.

Table I gives the values of the initial zeros of $J_0(x)$.

TABLE I

ZEROS OF $J_0(x)$

| N | $j_{0,n}$ |
|---|---|
| 1 | 2.4048 |
| 2 | 5.5201 |
| 3 | 8.6537 |
| 4 | 11.7915 |
| 5 | 14.9309 |

The sum in eq. (6) is infinite and not appropriate for an experiment that is to be perform in a finite length of time. Thus, it is appropriate to truncate this series as an approximation. This truncation removes components that are rapidly oscillating with the RF amplitude in a smoother estimation of the spin density as a function of RF amplitude. As long the RF amplitude is a reasonably behaved function can be mapped into the sensitive volume, the density as a function of RF amplitude can be mapped into the density as a function of position. For example, the preferred tool discussed about with reference to FIG. 2 is designed so that the RF amplitude used during transmission varies monotonically from a maximum in front of the tool to a minimum (almost 0) at the back of the tool. Thus a simple transform takes the spin density as a fiction of $\omega_1$ to a function of angle from front to back.

Referring now to FIG. 5, a flow chart for a first embodiment of the present invention is shown. Selection of a maximum number of terms $n_{max}$ for the Bessel function series in eq. (7) is made. This is based on experience and knowledge of the field gradient of the RF magnetic field of the tool. A practical constraint is the amount of acquisition time that can be spent in acquiring data. The value of n is initialized to zero 501 and incremented 502. A pulse length $\tau_1$ is determined from eq. (8) and the first zero of the zero-order Bessel function, i.e., 2.4048. A FID corresponding to the selected value of the pulse length is acquired 503. A check is made to see if the maximum number of pulses has been exceeded 505. If the answer is "no" 507, the value of n is incremented 502 and another pulse length is selected and a FID acquired. If the answer is "yes" 509, the resultant data, after transforming to the frequency domain, are inverse-Hankel-transformed 511 according to eq. (7) to give the spin-density as a function of the RF magnetic field (in the frequency domain). A simple mapping from RF magnetic field to the spatial location 513 is made using the known spatial variation of the RF field intensity. Once this step is done, it is a straightforward procedure to determine the portion of the signal that comes from inside the borehole (hence from the borehole fluid) and the portion of the signal that is outside the borehole. In the preferred hardware device discussed above with reference to FIG. 2, a predetermined cutoff in the RF magnetic field strength will separate the distribution into two parts. The part below the cutoff will correspond to the signal coming from the borehole and the part above the cutoff will correspond to the signal from the formation. Using the method described above, parameters of interest of the earth formation, such as spin density function can be determined.

An example of the RF field strength is shown in FIG. 5a. Shown therein is a RF magnetic field distribution for the device shown in FIG. 2. The azimuthal angle is from the front of the device to the back of the device. The zero in the axial is the symmetry axis of the device. In the units shown, the maximum $B_1$ is 0.022. For a given axial position, the RF magnetic field decays nearly uniformly to approximately zero at angles greater than about 100°.

The results can be improved further by using a caliper, preferably an acoustic caliper (not shown) to get an exact position of the tool and any washouts that may be present in the borehole wall. Adjusting the cutoff using the caliper measurements can correct for possible problems caused by washouts and/or improper tool positioning. For example, U.S. Pat. Nos. 5,638,337 and 5,737,277 to Priest teach methods for determining borehole geometry from acoustic caliper data. The methods taught by Priest or other suitable method may be used for determining the cutoff for the RF magnetic field.

A pulse sequence suitable for use with the invention described in the flow chart of FIG. 5 is shown in FIGS. 5b and 5c. Shown in FIG. 5b is an exemplary pulse sequence comprising three pulses 551, 553, 555 of duration $\tau_1$, $\tau_2$ and $\tau_3$ respectively with a wait time of TW in between. The resulting free induction decay signals 561, 563, 565 are shown in FIG. 5c. The $\tau$'s are chosen as discussed above and the maximum of the FID signal is used for analysis.

Another embodiment of the present invention uses spin-echo signals obtained using modified CPMG sequences. Hurlimann and Griffin shows that the asymptotic behavior of the echo amplitudes is, to the first order of approximation, identical to that of the FID after a single pulse. Consequently, it is possible to use the method of the present invention with modified CPMG sequences. This aspect of the invention is discussed with reference to FIG. 6.

Shown in FIG. 6 are a tipping pulse 601 having a length $\tau_a$ followed by a plurality of refocusing pulses 603 each having a length $\tau_b$. Also shown are spin echo signals 605 following the refocusing pulses. The flow chart of FIG. 7 illustrates how such spin-echo data are used to derive the desired properties of the formation.

Referring now to FIG. 7a, the value of n is initialized to zero 701 and incremented 703. Spin echo signals are acquired 705 using a modified CPMG sequence with a tipping pulse duration $\tau_a$ selected according to eq. (8). The pulse sequence for obtaining the spin echo signals are depicted in FIG. 7c. FIG. 7c shows a first modified CPMG sequence 751 of a tipping pulse $\tau_1$ followed by a plurality of refocusing pulses with a time interval TE between them. The refocusing pulses have a tip angle less than 180, as disclosed in U.S. Pat. No. 6,163,153 to Reiderman, et al. (having the same assignee as the present application). It should be noted that the method of the present invention can also be used with refocusing pulses with a tip angle of 180.

Going back to FIG. 7a, a check is made to see if more pulse sequences are to be applied 707. If the answer is "yes," n is incremented 703 and another pulse sequence is applied 705. This next pulse sequence is depicted by 753 in FIG. 7c and follows the first pulse sequence 751 by a wait time of TW. The next pulse sequence, as seen in FIG. 7c, has a tipping pulse with a tip angle of $\tau_2$. Returning to FIG. 7a, the process of acquiring additional pulse sequences is continued until there are no more sequences to be acquired 707. Thus, a set of data $S(\theta_{a,n},m)$ is collected where m is the echo number such that the echo occurs at time mTE where TE is the echo spacing, and $\theta_{a,n}$ is the tipping angle for the tipping pulse, $\tau_n$.

After the desired number of values of the tipping pulses have been selected, analysis of the echo signals begins at 709 with setting the echo index to 0 at 709, incrementing it by one 711 and summing all the pulse sequences over n for the m-th echo signal according to eqn. (7) 713. A check is made to see if there are any more values of m to be processed 715. The summed spin echo signals represent the spin density as a function of the RF field amplitude and echo time, $S(\omega_1,m)$. Keeping $\omega_1$ constant, these echo amplitudes can be inverted using techniques well known in the art and $S(\omega_1,m)$ becomes $S(\omega_1,T_2)$. In other words, a spin-density map as a function of RF magnetic field and $T_2$ 717 in FIG. 7b is produced. Next, the spin density is mapped to spatial locations 719 using the known distribution of RF field amplitude.

A convenient form for denoting the pulse sequence of FIG. 7c is the equation:

$$\left[ \tau_j - \frac{TE}{2} - (R - TE)_i - TW \right]_j$$

where TE is a time interval between refocusing pulses R, $\tau_j$ is a tipping pulse, TW is a wait time, i is the index of the number of refocusing pulses and j is the index of the number of CPMG (or modified CPMG) sequences acquired for a single tipping pulse. For a conventional CPMG sequence, the refocusing pulses have a 180 tipping angle. For a modified CPMG sequence, the tip angle of the refocusing pulse is less than 180.

In the analysis of the embodiments described above, it has been assumed that the transmit RF amplitude and the receive RF amplitudes are the same. In other words, the same coil is used for both transmitting and receiving. However, the invention is well-suited to use where different coils are used for transmitting and receiving, and such is an additional embodiment disclosed for the invention. In the general case, the spin density function in eqns. (6) and (7) may be replaced by:

$$f(\omega_1) \leftarrow \int d\omega_{1r} \omega_{1r} f(\omega_1, \omega_{1r}), \quad (9)$$

where $\omega_{1r}$ is the RF magnetic field generated by the current I in the receive coil and $f(\omega_1,\omega_{1r})$ is the spin density distribution as a function of both receive and transmit RF field amplitudes. The first two embodiments described are special cases of this general case.

The RF magnetic field distribution shown in FIG. 5a is seen to have a maximum for the exemplary NMR instrument discussed above at approximately 25 cm and 0 azimuth. Only one half of the distribution is shown in the figure, and the distribution for negative azimuth angles is substantially the same. Hence in the procedure discussed above, values from positive and negative azimuths will be combined. This fact would appear to present a problem to obtaining a complete azimuthal image of the formation properties. However, this is not the case as discussed next.

In another embodiment of the invention, measurements are made with a rotating tool. This additional embodiment can be accomplished easily in MWD applications where the NMR instrument is conveyed on a rotating bottom hole assembly (BHA) (not shown), measurements are taken during rotation of the BHA, and only a part of the image is retained. This retained data could be data from a sector of, for example, 15 on either side of the zero azimuth line, providing a partial image within a 30 sector. With continued rotation of the NMR instrument, measurements are repeated at additional rotational angles to provide additional sectors of imaged data. The complete image is then obtained as a composite of the individual sector images.

The problem noted above with respect to overlap of positive and negative azimuths about the symmetry direction is not a major problem because rotation of the instrument would occur in any case during the acquisition of the NMR signals, resulting in a certain amount of smear. For MWD implementation, the processor may be located in the BHA.

While the foregoing discloses several embodiments of the invention including the preferred embodiment, various modifications will be apparent to those skilled in the art. As this disclosure is written to those skilled in the art, it is intended that all variations within the scope and spirit of the appended claims be embraced by the foregoing disclosure.

What is claimed is:

1. A method determining a parameter of interest for a region of an earth formation using a nuclear magnetic resonance (NMR) instrument conveyed in a borehole, the method comprising:
   (a) producing a static magnetic field in said region;
   (b) transmitting a sequence of radio frequency (RF) pulses and producing an RF magnetic field in said region, said RF magnetic field having a spatially varying intensity in said region at least one of said RF pulses having a pulse length related to a zero of a Bessel function;
   (c) receiving NMR signals produced by said RF magnetic field; and
   (d) determining said parameter of interest using said received NMR signals.

2. The method of claim 1 wherein said said parameter of interest comprises at least one of (i) a spin density function, (ii) porosity, (iii) fluid content, (iv) permeability, (v) longitudinal relaxation time, and, (vi) transverse relaxation time.

3. The method of claim 1 wherein said NMR signals comprise free induction decay signals.

4. The method of claim 3 wherein determining said parameter of interest further comprises performing an inverse Hankel transform on said NMR signals.

5. The method of claim 4 wherein determining said parameter of interest further comprises using a spatial mapping to map a spin density to a spatial location.

6. The method of claim 5 further comprising determining spins associated with a portion of the region outside said borehole.

7. The method of claim 5 further comprising partitioning spins into azimuthal sectors.

8. The method of claim 1, wherein said sequence of RF pulses comprises tipping pulses, and refocusing pulses, and wherein said NMR signals comprise spin echo signals.

9. The method of claim 8 wherein said sequence of RF pulses is of the form:

$$\left[\tau_j - \frac{TE}{2} - (R - TE)_i - TW\right]_j$$

where TE is a time interval between refocusing pulses R, $\tau_j$ is a tipping pulse, TW is a wait time, i is the index of the number of refocusing pulses, and j is the index of the number of CPMG (or modified CPMG) sequence acquired for a single tipping pulse.

10. The method of claim 9 wherein determining said parameter of interest further comprises summing the spin echo signals resulting from said sequence of RF pulses over the index j for a selected value of i.

11. The method of claim 10 wherein said summing is a weighted summing.

12. The method of claim 11 wherein determining said parameter of interest further comprises using a spatial mapping to map a spin density to a spatial location.

13. The method of claim 12 further comprising determining spins associated with a portion of the region outside the borehole.

14. The method of claim 12 further comprising partitioning spins into azimuthal sectors.

15. The method of claim 1 further comprising repeating (a)–(d) for a number of different azimuthal orientations of said instrument.

16. The method of claim 15 further conveying said NMR instrument into said borehole on a bottom hole assembly.

17. The method of claim 1 wherein said Bessel function is a Bessel function of zero order and first kind.

18. An apparatus for determining a parameter of interest of a region of an earth formation comprising:
   (a) a magnet producing a static magnetic field within the region;
   (b) a transmitter transmitting a sequence of radio frequency (RF) pulses and generating a RF magnetic field in said region, said RF magnetic field having a spatially-varying intensity in said region,
   (c) a processor controlling said transmitter and defining at least one of said RF pulses to have a pulse length related to a zero of a Bessel function;
   (d) a receiver receiving NMR signals produced by said RF magnetic field; and
   (e) a processor determining said parameter of interest from said NMR signals.

19. The apparatus of claim 18 wherein said said parameter of interest comprises at least one of (i) a spin density function, (ii) porosity, (iii) fluid content, (iv) permeability, (v) longitudinal relaxation time, and, (vi) transverse relaxation time.

20. The apparatus of claim 18 wherein said NMR signals comprise free induction decay signals.

21. The apparatus of claim 18 wherein sequence of RF pulses comprise tipping pulses and refocusing pulses and wherein said NMR signals comprise spin echo signals.

22. The apparatus of claim 18 wherein said processor in (e) is configured so as to determine a spin density as a function of said RF field intensity.

23. The apparatus of claim 22 wherein said processor is configured to transform said spin density to a spatial location.

24. The apparatus of claim 22 wherein said sequence of RF pulses is of the form:

$$\left[\tau_j - \frac{TE}{2} - (R - TE)_i - TW\right]_j$$

where TE is a time interval between refocusing pulses R, $\tau_j$ is a tipping pulse, TW is a wait time, i is the index of the number of refocusing pulses and j is the index of the number of CPMG (or modified CPMG) sequence acquired for a single tipping pulse.

25. The apparatus of claim 18 wherein the same antenna is used for transmitting said RF pulses and receiving said NMR signals.

26. The apparatus of claim 18 wherein said processor in (c) and said processor in (e) are the same.

27. The apparatus of claim 18 wherein said Bessel function is a Bessel function of zero order and first kind.

28. A method of composing a radio frequency (RF) pulse sequence for use in a nuclear magnetic resonance (NMR) apparatus, the method comprising:
   (a) defining a length of at least one pulse of the RF pulse sequence based on a zero of a Bessel function;
   (b) producing a RF field with said RF pulse sequence; and
   (c) analyzing NMR signals resulting from the produced RF field.

29. The method of claim 28 wherein said Bessel function is a zero order Bessel function of the first kind.

30. A nuclear magnetic resonance (NMR) apparatus comprising:
   (a) a processor that:
      (i) defines a length of at least one pulse of a radio frequency RF pulse sequence based on a zero of a Bessel function, and
      (ii) pulses a transmitter with the RF pulse sequence, wherein the transmitter produces a RF field;
   (b) a receiver which receivers NMR signals resulting from the RF field;
   (c) a processor which analyzes the received NMR signals.

31. The NMR apparatus of claim 30 wherein the Bessel function is a Bessel function of zero order and the fist kind.

* * * * *